(12) United States Patent
Hillbratt et al.

(10) Patent No.: US 9,158,891 B2
(45) Date of Patent: Oct. 13, 2015

(54) MEDICAL DEVICE DIAGNOSTICS USING A PORTABLE DEVICE

(71) Applicant: COCHLEAR LIMITED, Macquarie University (AU)

(72) Inventors: Martin Evert Gustaf Hillbratt, Lindome (SE); Mats Erik Hojlund, Molnlycke (SE)

(73) Assignee: COCHLEAR LIMITED, Macquarie University, NSW (AU)

( * ) Notice: Subject to any disclaimer, the term of this patent is extended or adjusted under 35 U.S.C. 154(b) by 315 days.

(21) Appl. No.: 13/768,807

(22) Filed: Feb. 15, 2013

(65) Prior Publication Data

US 2014/0233743 A1    Aug. 21, 2014

(51) Int. Cl.
*H04R 25/00* (2006.01)
*G06F 19/00* (2011.01)
*G06F 11/00* (2006.01)

(52) U.S. Cl.
CPC ............ *G06F 19/3412* (2013.01); *G06F 11/00* (2013.01); *H04R 2460/13* (2013.01); *H04R 2499/11* (2013.01)

(58) Field of Classification Search
CPC .... G06F 19/3406; H04R 25/00; H04R 25/30; H04R 2460/13; H04R 2499/11
See application file for complete search history.

(56) References Cited

U.S. PATENT DOCUMENTS

| | | | | |
|---|---|---|---|---|
| 2002/0191800 | A1* | 12/2002 | Armstrong | 381/60 |
| 2007/0286429 | A1* | 12/2007 | Grafenberg et al. | 381/60 |
| 2008/0240452 | A1* | 10/2008 | Burrows et al. | 381/60 |
| 2008/0253579 | A1* | 10/2008 | Cronin et al. | 381/60 |
| 2011/0009770 | A1* | 1/2011 | Margolis et al. | 600/559 |
| 2013/0243210 | A1* | 9/2013 | Roeck et al. | 381/60 |

OTHER PUBLICATIONS

Petr, Nalevka, "Smartphones For In-Home Diagnostics in Telemedicine", International Journal of Medical and Biological Sciences, Jun. 2012, p. 36-40.

* cited by examiner

*Primary Examiner* — Brenda Bernardi (57) ABSTRACT

Systems, methods, and apparatuses may be used to test devices using a portable device. A portable device is a tablet computer, a smart phone, or other type of device. In embodiments, the different components of the portable device are utilized to perform tests on a medical device such as a hearing prosthesis or other type of medical device. For example, portable device components such as accelerometers, magnetometers, gyroscopes, microphones, speakers, etc. are used to provide testing stimuli and/or record the responses from the hearing prosthesis to the testing stimuli. The portable device is used to generate testing stimulus and record the response from the device being tested using the various components of the portable device. Analysis of the output of the medical device can be performed to determine a remedy to improve operation of the device.

30 Claims, 11 Drawing Sheets

MEDICAL DEVICE DIAGNOSTICS USING A PORTABLE DEVICE

BACKGROUND

Auditory prostheses, such as bone conduction devices, convert a received sound into vibrations. The vibrations are transferred through teeth and/or bone to the cochlea, causing generation of nerve impulses, which result in the perception of the received sound. Bone conduction devices are suitable to treat a variety of types of hearing loss and may be suitable for individuals who cannot derive sufficient benefit from acoustic hearing aids, cochlear implants, etc., or for individuals who suffer from stuttering problems. Bone conduction devices may be coupled to a user using a direct percutaneous implant and abutment, or using transcutaneous solutions, which can contain an active or passive implant component, or other mechanisms to transmit sound vibrations through the skull bones, such as through vibrating the ear canal walls or the teeth. In many cases, it is useful to test such a device to ensure it is working properly. It is with respect to this general environment that embodiments of the present technology have been contemplated.

SUMMARY

Embodiments disclosed herein relate to systems, methods, and apparatuses that are used to test medical devices, for example, bone conduction devices or other hearing aids or devices, using a portable device. A portable device is a tablet computer, a smart phone, or other type of device that is commonly used. In embodiments, the components of the portable device are utilized to test a medical device. This allows a recipient or user of a device to perform diagnostic tests on a device to ensure it is working correctly without having to use specialized equipment that may only be available to a clinician or a device manufacturer.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The systems and methods disclosed herein provide a method that can be performed by a portable device, such as, but not limited to, a smartphone or a tablet, that performs diagnostic testing on a medical device, such as a hearing prosthesis or other device that requires diagnostic testing. This allows a device recipient or user to quickly ensure that her device is properly working without having to obtain specialized equipment or visit a specialized technician. If problems are detected based upon the diagnostic testing, the methods disclosed herein provide for displaying instructions regarding remedies to correct problems with the device or optimize the device settings.

Figure 1:
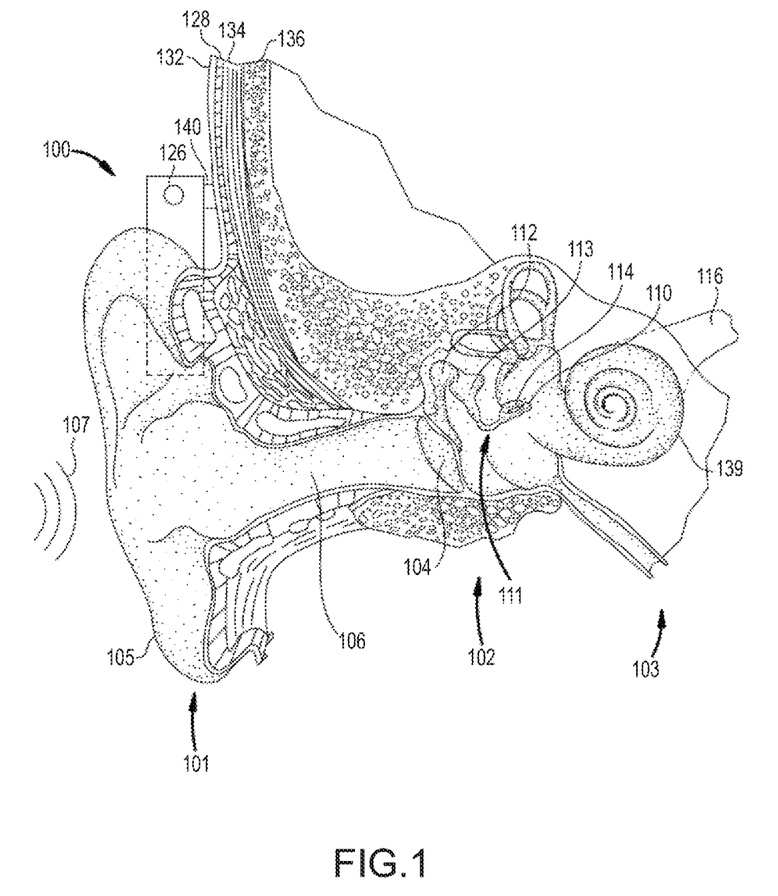
FIG. 1 is a perspective view of an example of a percutaneous bone conduction device 100 positioned behind outer ear 101 of the recipient and comprises a sound input element 126 to receive sound signals 107.
Figure 2:
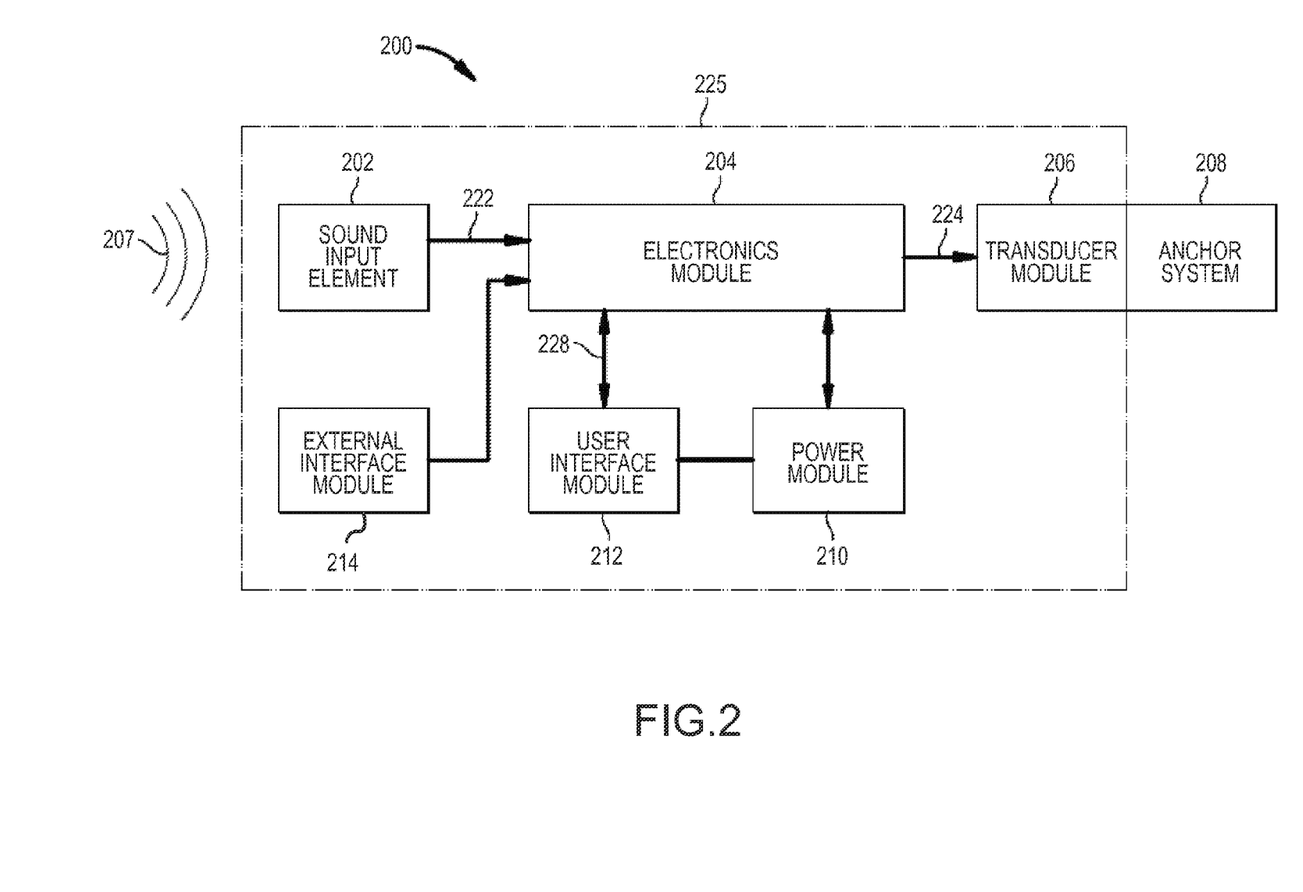
FIG. 2 is functional block diagram of one example of a bone conduction device 200.
Figure 3:
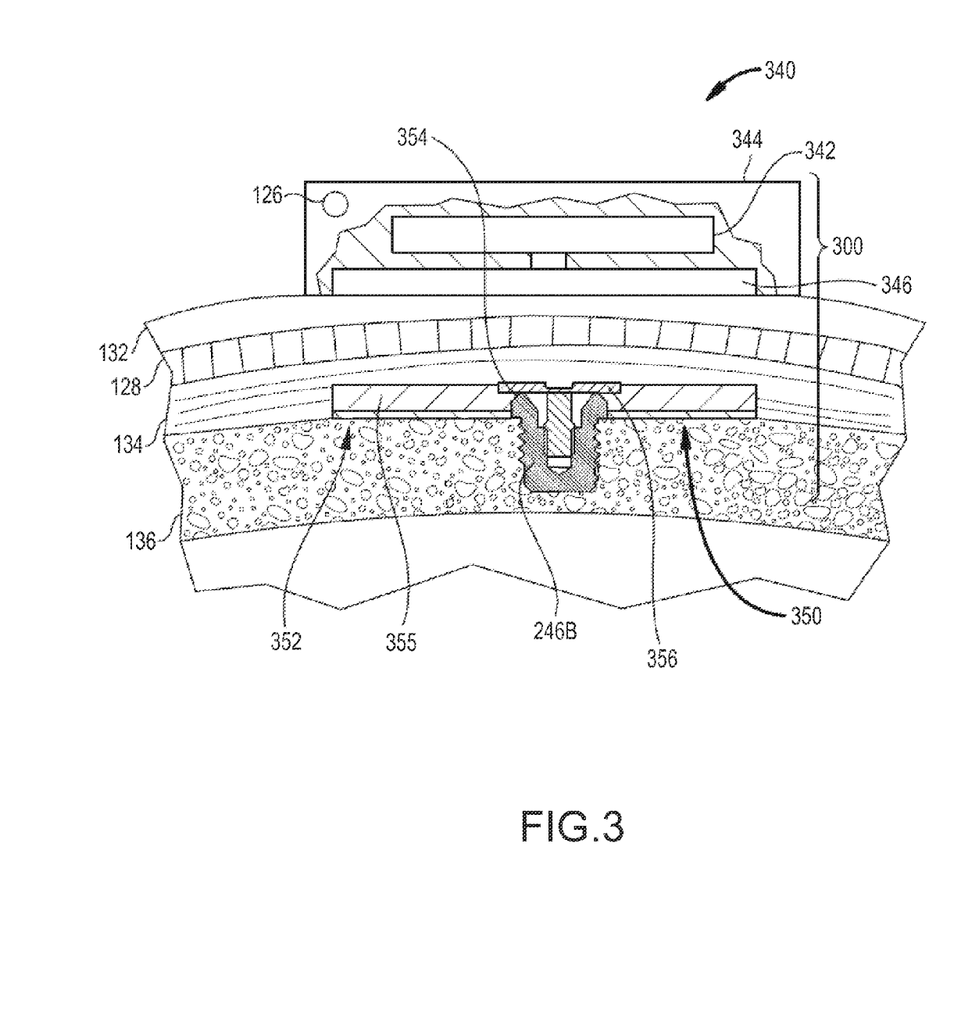
FIG. 3 depicts an example of a transcutaneous bone conduction device 300.
Figure 4:
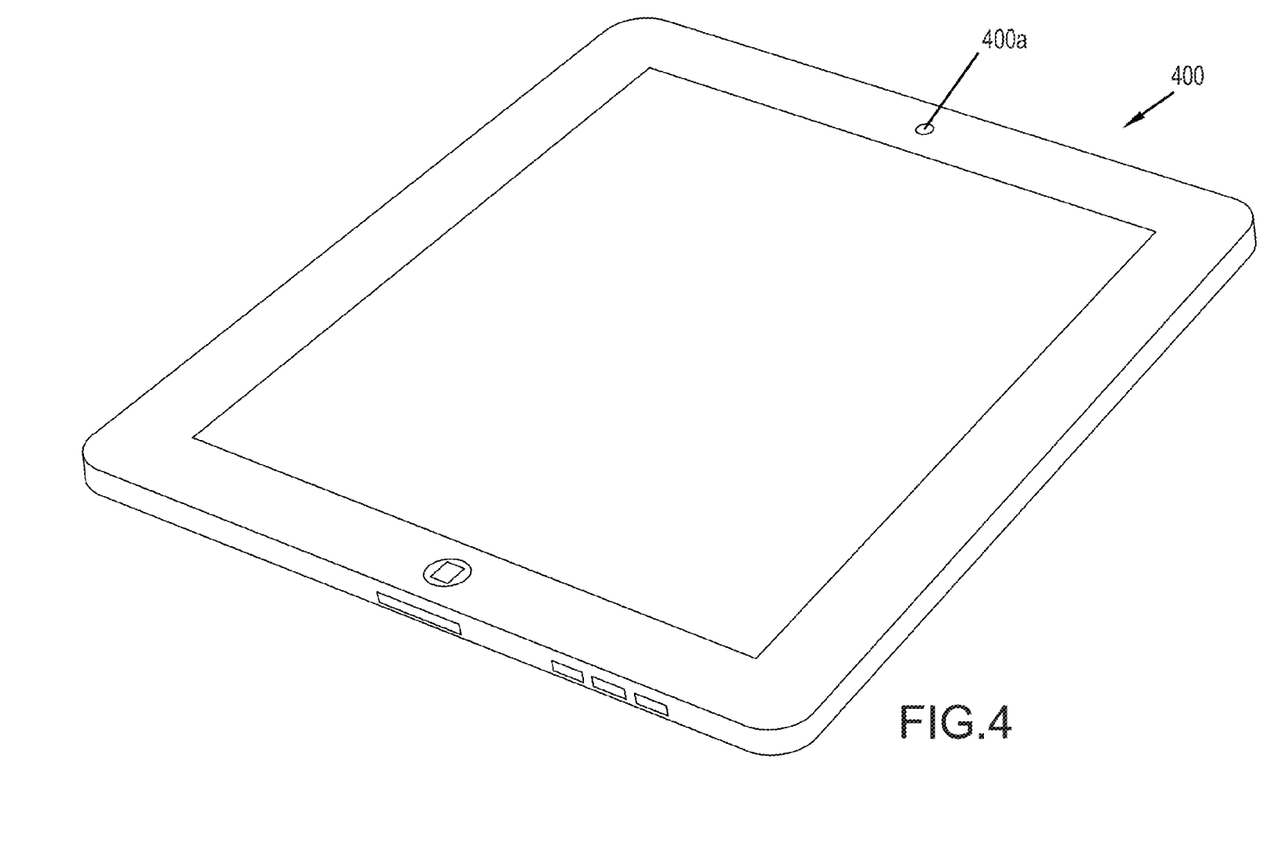
FIG. 4 is an example of a portable device 400 that can be used to perform diagnostic tests.

While the technologies disclosed herein have particular application in the bone conduction devices depicted in FIGS. 1-3, it will be appreciated that the systems, methods, and apparatuses disclosed can be employed to perform device diagnostics on other types of hearing prostheses. For example, the embodiments disclosed herein can be used to perform diagnostics on components of traditional hearing aids, hearing prostheses, active transcutaneous bone conduction devices, passive transcutaneous devices, middle ear devices, tooth-anchored hearing devices, etc. Furthermore, the embodiments disclosed herein may be practiced to perform diagnostics on medical devices other than hearing prostheses, or may be used in conjunction with devices that treat conditions independent of hearing loss, such as tinnitus. Accordingly, the technologies disclosed herein will be described generally in the context of medical devices. Certain aspects of the technology however, for example, the fixtures identified in FIGS. 4-4C are described in the context of bone conduction devices.

FIG. 1 is a perspective view of a percutaneous bone conduction device 100 positioned behind outer ear 101 of the recipient and comprises a sound input element 126 to receive sound signals 107. The sound input element 126 can be a microphone, telecoil or similar. In the present example, sound input element 126 may be located, for example, on or in bone conduction device 100, or on a cable extending from bone conduction device 100. Also, bone conduction device 100 comprises a sound processor (not shown), a vibrating actuator (e.g., electromagnetic, piezo electric, electrostrictive, etc.), and/or various other operational components.

More particularly, sound input device 126 converts received sound signals into electrical signals. These electrical signals are processed by the sound processor. The sound processor generates control signals that cause the actuator to vibrate. In other words, the actuator converts the electrical signals into mechanical force to impart vibrations to skull bone 136 of the recipient.

Bone conduction device 100 further includes coupling apparatus 140 to attach bone conduction device 100 to the recipient. In the example of FIG. 1, coupling apparatus 140 is attached to an anchor system (not shown) implanted in the recipient. An exemplary anchor system (also referred to as a fixation system) may include a percutaneous abutment fixed to the recipient's skull bone 136. The abutment extends from skull bone 136 through muscle 134, fat 128 and skin 132 so that coupling apparatus 140 may be attached thereto. Such a percutaneous abutment provides an attachment location for coupling apparatus 140 that facilitates efficient transmission of mechanical force.

A functional block diagram of one example of a bone conduction device 200 is shown in FIG. 2. Sound 207 is received by sound input element 202. In some arrangements, sound input element 202 is a microphone configured to receive sound 207, and to convert sound 207 into electrical signal 222. Alternatively, sound 207 is received by sound input element 202 as an electrical signal.

As shown in FIG. 2, electrical signal 222 is output by sound input element 202 to electronics module 204. Electronics module 204 is configured to convert electrical signal 222 into adjusted electrical signal 224. As described below in more detail, electronics module 204 may include a sound processor, control electronics, transducer drive components, and a variety of other elements.

As shown in FIG. 2, transducer 206 receives adjusted electrical signal 224 and generates a mechanical output force in the form of vibrations that is delivered to the skull of the recipient via anchor system 208, which is coupled to bone conduction device 200. Delivery of this output force causes motion or vibration of the recipient's skull, thereby activating the hair cells in the recipient's cochlea (not shown) via cochlea fluid motion.

FIG. 2 also illustrates power module 210. Power module 210 provides electrical power to one or more components of bone conduction device 200. For ease of illustration, power module 210 has been shown connected only to user interface module 212 and electronics module 204. However, it should be appreciated that power module 210 may be used to supply power to any electrically powered circuits/components of bone conduction device 200.

User interface module 212, which is included in bone conduction device 200, allows the recipient to interact with bone conduction device 200. For example, user interface module 212 may allow the recipient to adjust the volume, alter the speech processing strategies, power on/off the device, etc. In the example of FIG. 2, user interface module 212 communicates with electronics module 204 via signal line 228.

Bone conduction device 200 may further include external interface module that may be used to connect electronics module 204 to an external device, such as a fitting system. Using external interface module 214, the external device, may obtain information from the bone conduction device 200 (e.g., the current parameters, data, alarms, etc.) and/or modify the parameters of the bone conduction device 200 used in processing received sounds and/or performing other functions.

In the example of FIG. 2, sound input element 202, electronics module 204, transducer 206, power module 210, user interface module 212, and external interface module have been shown as integrated in a single housing, referred to as housing 225. However, it should be appreciated that in certain examples, one or more of the illustrated components may be housed in separate or different housings. Similarly, it should also be appreciated that in such examples, direct connections between the various modules and devices are not necessary and that the components may communicate, for example, via wireless connections.

FIG. 3 depicts an example of a transcutaneous bone conduction device 300 that includes an external device 340 and an implantable component 350. The transcutaneous bone conduction device 300 of FIG. 3 is a passive transcutaneous bone conduction device in that a vibrating actuator 342 is located in the external device 340. Vibrating actuator 342 is located in housing 344 of the external component, and is coupled to plate 346. Plate 346 may be in the form of a permanent magnet and/or in another form that generates and/or is reactive to a magnetic field, or otherwise permits the establishment of magnetic attraction between the external device 340 and the implantable component 350 sufficient to hold the external device 340 against the skin of the recipient.

In one example, the vibrating actuator 342 is a device that converts electrical signals into vibration. In operation, sound input element 126 converts sound into electrical signals. Specifically, the transcutaneous bone conduction device 300 provides these electrical signals to vibrating actuator 342, or to a sound processor (not shown) that processes the electrical signals, and then provides those processed signals to vibrating actuator 342. The vibrating actuator 342 converts the electrical signals (processed or unprocessed) into vibrations. Because vibrating actuator 342 is mechanically coupled to plate 346, the vibrations are transferred from the vibrating actuator 342 to plate 346. Implanted plate assembly 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient. Accordingly, vibrations produced by the vibrating actuator 342 of the external device 340 are transferred from plate 346 across the skin to plate 355 of plate assembly 352. This may be accomplished as a result of mechanical conduction of the vibrations through the skin, resulting from the external device 340 being in direct contact with the skin and/or from the magnetic field between the two plates. These vibrations are transferred without penetrating the skin with a solid object such as an abutment as detailed above with respect to a percutaneous bone conduction device.

As may be seen, the implanted plate assembly 352 is substantially rigidly attached to bone fixture 246B in this example. As indicated above, any other bone fixture may be used instead of bone fixture 246B in this and other examples. In this regard, implantable plate assembly 352 includes through hole 354 that is contoured to the outer contours of the bone fixture 246B. This through hole 354 thus forms a bone fixture interface section that is contoured to the exposed section of the bone fixture 246B. In an example, the sections are sized and dimensioned such that at least a slip fit or an interference fit exists with respect to the sections. Plate screw 356 is used to secure plate assembly 352 to bone fixture 246B. As can be seen in FIG. 3, the head of the plate screw 356 is larger than the hole through the implantable plate assembly 352, and thus the plate screw 356 positively retains the implantable plate assembly 352 to the bone fixture 246B. The portions of plate screw 356 that interface with the bone fixture 246B substantially correspond to an abutment screw detailed in greater detail below, thus permitting plate screw 356 to readily fit into an existing bone fixture used in a percutaneous bone conduction device. In an example, plate screw 356 is configured so that the same tools and procedures that are used to install and/or remove an abutment screw (described below) from bone fixture 246B can be used to install and/or remove plate screw 356 from the bone fixture 246B.

FIG. 4 is an embodiment of a portable device 400 that can be used to perform diagnostic tests on a medical device. In embodiments, a portable device 400 can be a smartphone, a tablet computing device, a laptop computing device, or other type of portable computing device, as will be described in more detail in FIGS. 6 and 7. In embodiments, the various components of the portable device 400 can be utilized to perform a diagnostics test by administering one or more tests, collecting test results from a medical device, and analyzing the testing results to produce and/or present diagnostic results. One or more diagnostics tests can be administered by the portable device 400 by using one of the portable device's output components. For example, the portable device 400 can play a test sound using a loudspeaker, display a test or testing instructions using a display, or communicate directly with the medical device being tested using a Bluetooth connection, a radio frequency ("RF") signal, or other means of communication. The portable device 400 can collect test results from a medical device using various input components that are part of the portable device 400. For example, the portable device 400 can record output from a medical device using a microphone 400a, magnetometer, accelerometer, gyroscope, camera, touch-sensitive screen, or other component. In embodiments, the portable device 400 can also collect data by communicating directly from a medical device via a Bluetooth connection, RF signal, or other means of communication.

Upon collecting the testing results, the portable device 400 can analyze the results of the tests. In one embodiment, the analysis may be performed locally by evaluating the testing data using a combination of software and/or hardware on the portable device 400. In another embodiment, the portable device 400 can transmit the test results to another device or system for analysis. In such embodiments, the portable device 400 can communicate with a remote device, such as, but not limited to, a server over a network. Example networks that may be used to facilitate the communication can be a local area network ("LAN"), wide area network ("WAN"), a cellular network, a plain old telephone service ("POTS") network, the Internet, or any other type of network capable of facilitating the communication of data between multiple devices. In such embodiments, a remote device may perform analysis on the test data and return results of the analysis to the portable device 400 via the network. Upon analyzing the results, either locally on the portable device 400 or by a remote device, results of the testing can be generated. The results can include test results, suggestions for fixing an identified problem with the medical device, instruction on how to service and/or tune the medical device, instructions on performing maintenance on the medical device, or any other type of results. The instructions can be provided to a user via one or more of the portable device's 400 output components. For example, the testing results and/or additional information can be displayed on the portable device's 400 display, audibly played using a loudspeaker, or otherwise provided to another device for presentation or storage.

Figure 4A:
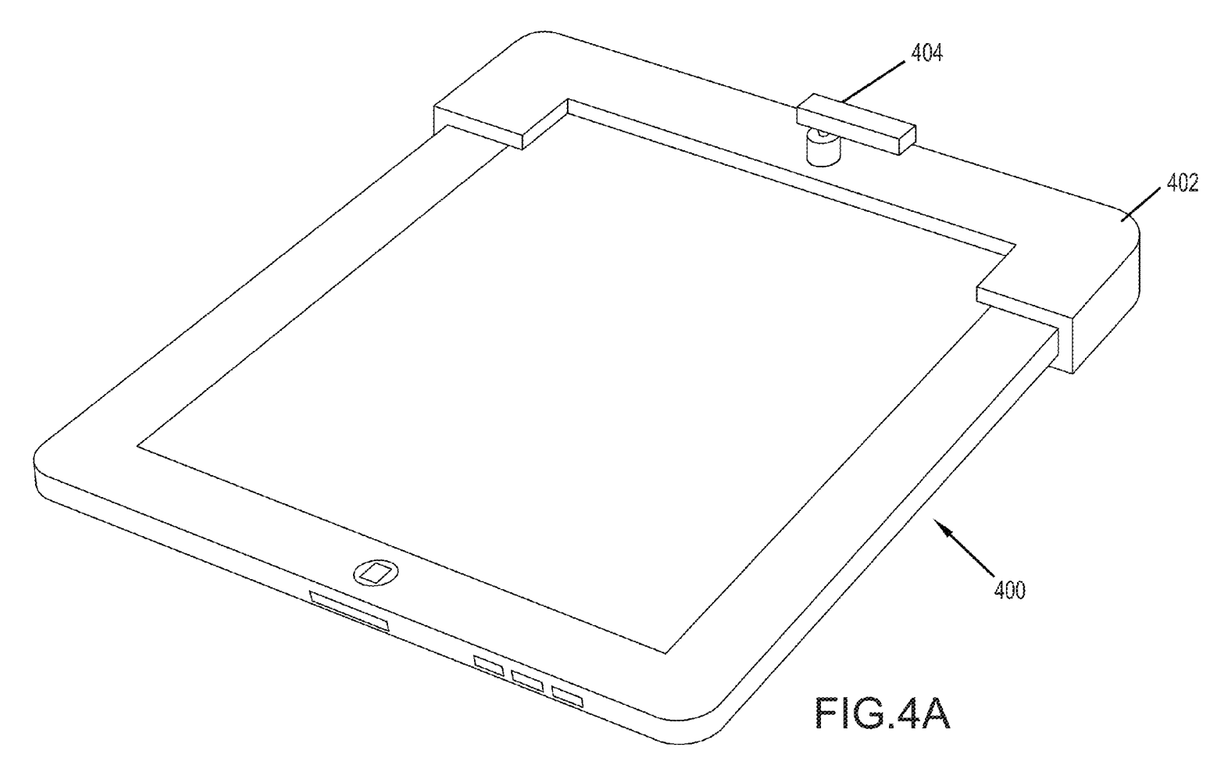
FIG. 4A is an embodiment of a fixture 402 that may be employed with the portable device to perform diagnostics testing.
Figure 4B:
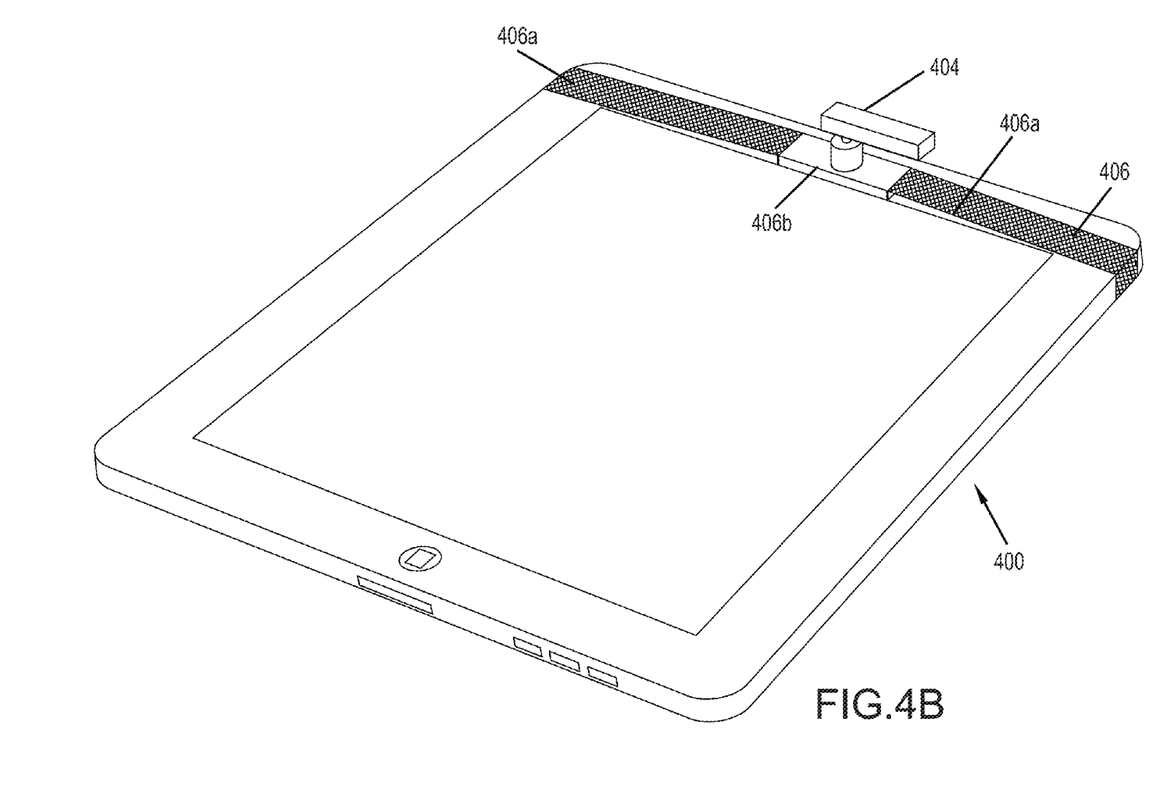
FIG. 4B is yet another embodiment of a fixture 406 that is used to secure a device 404 to a portable device 400.
Figure 4C:
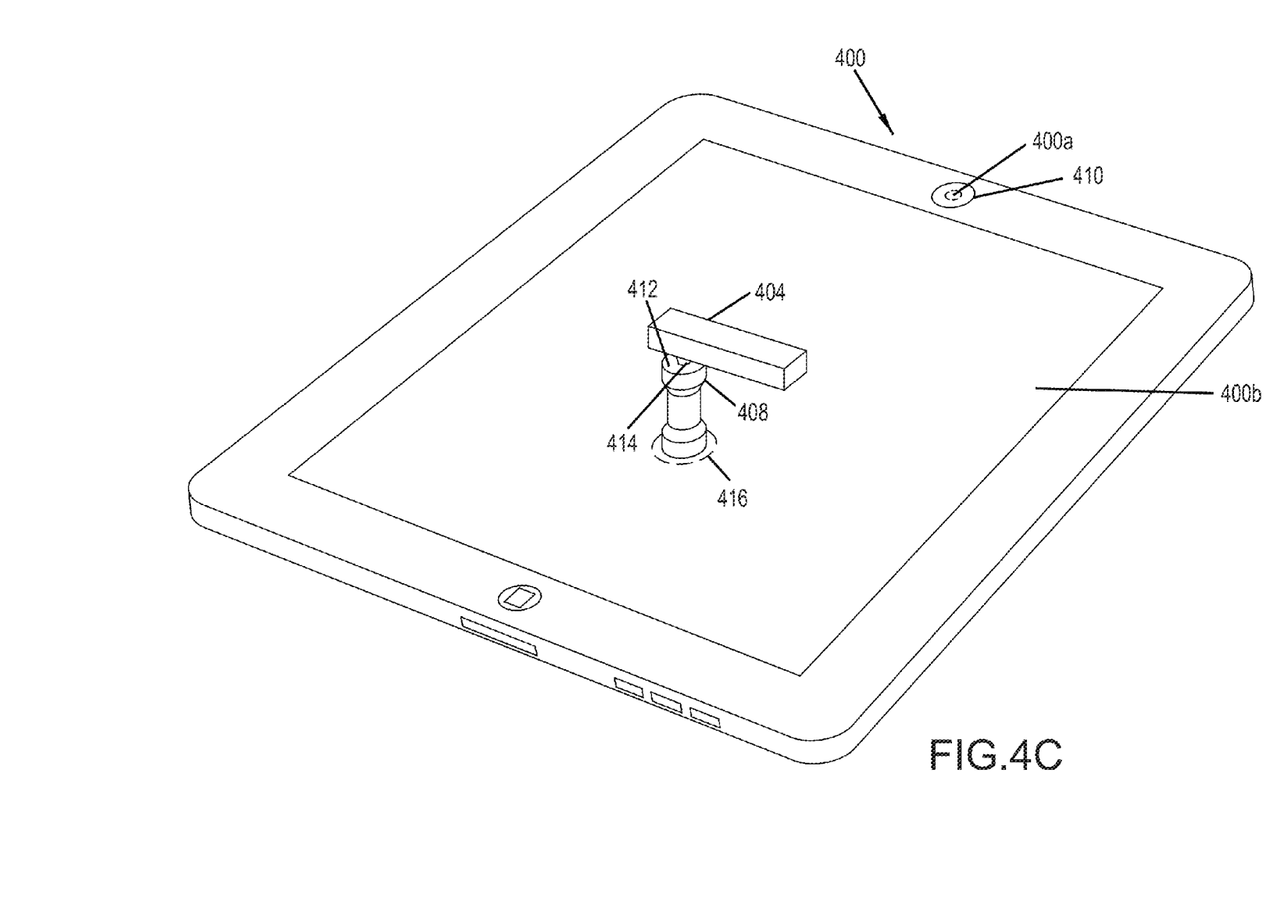
FIG. 4C is an alternate embodiment of a fixture 408 that is used to secure a device.

FIGS. 4A-4C depict various embodiments of fixtures that may be used to in conjunction with a portable device 400 and a medical device 404. In these figures, the medical 404 device is a bone conduction device. FIG. 4A depicts a fixture 402 that may be employed with the portable device 400 to perform diagnostics testing on a bone conduction device 404. Fixture 402 is an apparatus that can be coupled to the portable device 400. In the illustrated embodiment, fixture 402 is coupled to the portable device 400 by fitting over the edge of the portable device 400. In embodiments, fixture 402 includes a substantially U-shaped channel adapted to receive at least a portion of an edge of the portable device 400. Fixture 400 can also include a cover for covering a component of the portable device 400, such as a microphone on the portable device 400. In FIG. 4A, the entire fixture 402 covers the entire portion of the portable device 400 where the microphone is located. Accordingly, a discrete cover is not necessarily required. In certain embodiments, however, the cover may be a projection that extends from a portion of the fixture 402. Covering the device microphone blocks out ambient noise that may interfere with the collection of test results while still allowing the microphone to receive the vibrational output of the bone conduction device 404. Fixture 402 may cover the microphone of the portable device 400 to block external sound from being received by the microphone; however, the vibrations generated by the device 400 will still be transmitted through the fixture 402 and casing of the portable device 404 and be picked up by the microphone.

In other embodiments, fixture 402 can be coupled to the portable device via other means, such as by a clamping mechanism, an adhesive, etc. Fixture 402 may be used to secure a medical device. Securement can include inserting a portion of the device 404 into an opening defined by the fixture 402. Especially in the context of a bone conduction device, securing the device 404 provides for better testing and better collection of the testing results. For example, since the output of the bone conduction device 404 is a mechanical output (i.e., vibrations), fixture 402 provides that the device 404 will remain secured relative to the portable device 400 while it is generating mechanical output. In embodiments, fixture 402 can also be designed to secure device 404 to an optimal location for testing by the portable device 400.

FIG. 4B is yet another embodiment of a fixture 406 that is used to secure a device 404 to a portable device 400. The fixture 404 includes a plurality of clips or straps 406a, which may be elastic or rigid. The straps 406a are coupled at a microphone cover 406b, which also serves as a mounting base for the bone conduction device 404. In embodiments, fixture 406 can also be clipped or otherwise secured to the portable device 400 to optimize placement of the device 404 for testing. In alternate embodiments, fixture 406 includes a clamp adapted to secure the fixture to the portable device 400.

FIG. 4C is an alternate embodiment of a fixture 408 that is used to secure a device 404 to a portable device 400 for testing. In the illustrated embodiment, fixture 408 is a rigid plastic test rod. In the illustrated embodiment, fixture 408 is adhered to the display 400b of the portable device 400 rather than fitting over the edge or clipping to the portable device 400. In embodiments, fixture 408 can simply rest on the portable device 400. Here, however, the contacting surface of the fixture 408 can be secured to the display 400b of the portable device 400 using a releasable adhesive. Prior to use, the releasable adhesive is covered by a contact pad that may be removed to expose the adhesive. The contact pad 410 may then be utilized to cover the microphone 400a during testing. A device interface 412 (in this case, an upper surface of the fixture 404) can also define a receiver or opening 414 for receiving a portion of the device 404. The receiver 414 can be fitted for a specific type of device. For example, the receiver 414 may be an abutment fitted to receive a portion of the device 404, such as, but not limited to, the implant of a bone conduction device. In embodiments where the fixture 408 is placed on the portable device 400, the portable device 400 provides a graphical indication 416 on its display 400b to identify a location that the fixture 408 should be placed. In embodiments, the graphical indication 416 identifies an area that provides for optimal testing results. As such, the location of the graphical indication 416 can depend on the location and/or capabilities of the portable device components. The placement of graphical indication 416 can vary depending on the type of portable device 400. Alternatively, a suction element may be used in lieu of an adhesive.

While FIGS. 4A-4C provide specific examples of different fixtures that may be used to secure a device to a portable device for testing, other types of fixtures may be employed to secure a medical device to a portable device without departing from the scope of the present disclosure. For example, any type of fitting comprising a body with an interface for a medical device may be used. In embodiments, the body of the fixture comprises a vibration-conductive material that can be used to transmit mechanical output from, e.g., a bone conduction device, to the one or more components of the portable device.

Figure 5:
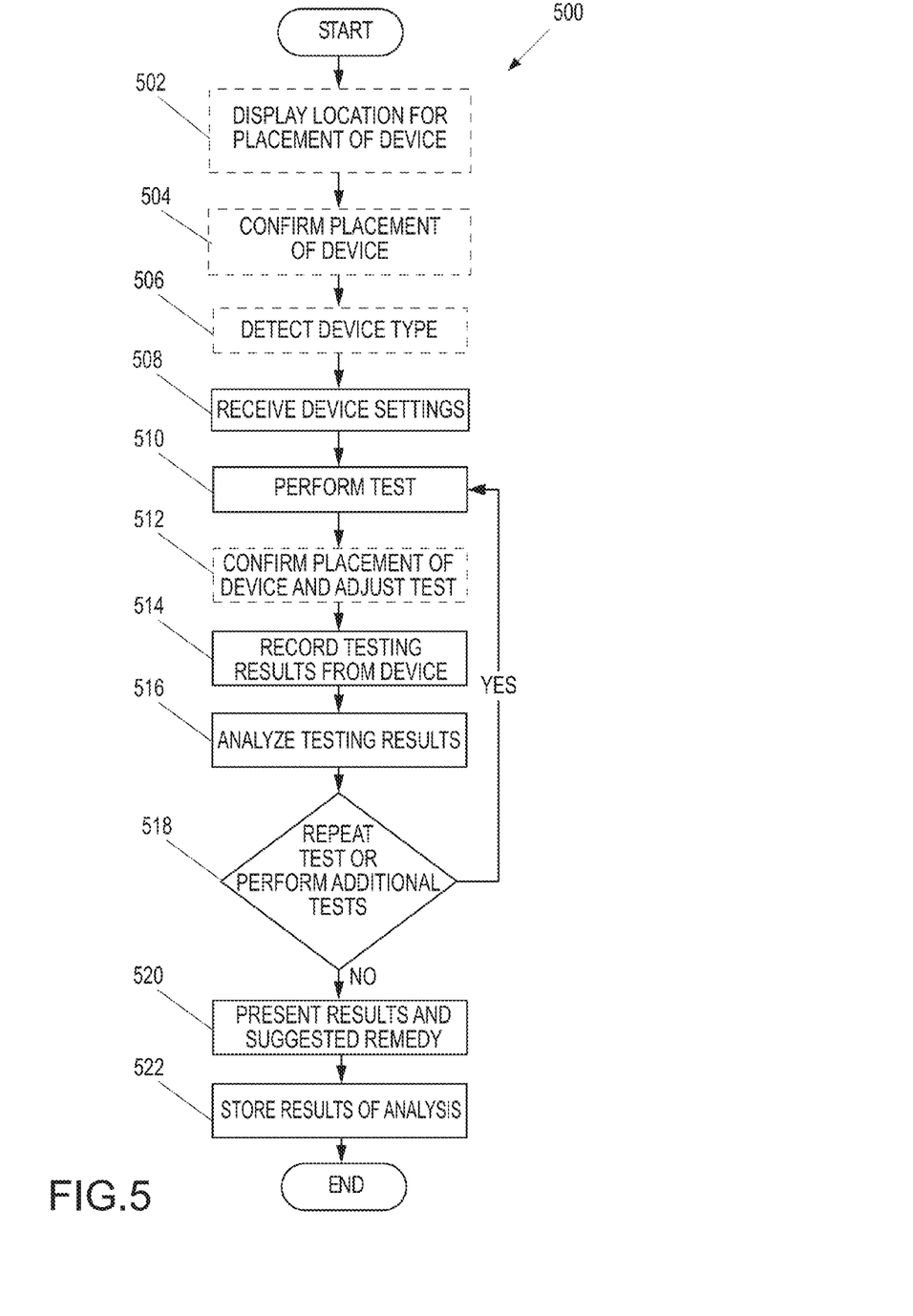
FIG. 5 is an embodiment of a method 500 to perform diagnostic testing on a device.

Having described the various embodiments of fixtures that can be used with a portable device to perform diagnostic testing, the disclosure will now describe embodiments of methods that can be executed by the portable device to performing diagnostic testing. FIG. 5 is an embodiment of a method 500 to perform diagnostic testing on a device such as a hearing prosthesis or other medical device. The method 500 can be performed by a portable device, a portable device in combination with one or more remote devices, or by one or more general computing devices. The operations described in the method 500 may be performed by software, hardware, or a combination of software and hardware. In one embodiment, the operations described with respect to the method 500 are completely performed by the portable device. In other embodiments, the operations described as part of method 500 are performed by multiple devices communicating over a network. For example, some of the operations of method 500 can be performed by a portable device while other operations are performed by a remote device communicating with the portable device via a network. In embodiments, testing stimuli is provided using various components of a portable device. For example, testing stimuli can be provided by a speaker, head set, inbuilt generator, audio cable, and/or wireless interface of the portable device. In embodiments, components of the portable device are also used to record the response to the testing stimulus of the device being tested. For example, a gyroscope, magnetometer, accelerometer, microphone and/or microphone can be employed to record responses to the testing stimuli.

The method 500 begins with the optional operation of displaying a location for placement of a fixture and/or device for testing. For example, in embodiments where a fixture is used to place a medical device on a portable device, such as fixture 408 illustrated in FIG. 4C, the portable device can display an area in which to place the fixture to perform the testing, for example, on the display screen. In embodiments, the area displayed is determined based upon the characteristics of the portable device. For example, the displayed area can be determined based upon the location of various different components of the portable device performing the test, the capabilities of the portable device performing the test, or based upon various other characteristics of the portable device. Flow continues to optional operation 504, where a determination is made as to whether the device is correctly placed on the portable device for testing. In one embodiment, a magnetometer that is part of the portable device can be used to detect the placement of the device and ensure it is placed in the correct location. In another embodiment, other components, such as a gyroscope or touch screen can detect whether the device is correctly placed for testing. Additionally, or alternatively, the portable device can confirm placement by querying the medical device or user for acknowledgement that the medical device is ready to test, without specifically identifying a precise location.

Flow continues to operation 506 where an optional determination is made as to the type of the device being tested. For example, the method 500 detects the type of device at operation 506. Various different types of devices can be tested using the method 500, such as bone conduction devices or standard hearing aids. Additionally, other types of medical devices may be tested using the method 500. Because different types of devices can require different types of testing, the method 500 detects the type of device before performing the test. Detection can be accomplished using a variety of different approaches. In one embodiment, the method 500 can automatically determine the type of device being testing using one or more components of a portable device. For example, a magnetometer can be used to detect a component of the medical device, such as a coil, and identify the type of device depending on the detected component. In another embodiment, the detection can be performed by receiving input from a user. In such an embodiment, a user interface can be displayed on the portable device screen. The user interface can receive input from a user indicating the type of device. For example, the user interface can display a list of devices and receive a selection of one of the devices from the list. In an alternate embodiment, the user interface can receive other type of input from a user, such as text or audio commands that indicate the type of device being tested.

Upon detecting the device type, flow continues to operation 508 where the method 500 receives or otherwise determines device settings. The device settings can be used to determine the type of testing to perform on the device. For hearing prostheses, for example, initial gain settings are determined along with other settings. The device settings can be received as input to a user interface. In another embodiment, the device settings can be automatically detected by communicating with the device using a wireless interface, such as a Bluetooth connection or a RF signal, or detected using one or more of the components of the portable device.

Upon receiving or otherwise determining the device settings, flow continues to operation 510 where a test is performed on the device. In embodiments, one or more components of the portable device capable of providing output are used to perform the test. For example, in one embodiment, the portable device speaker is used to play one or more test sounds to a hearing prosthesis. In another embodiment, the portable device can perform the test using a display, using a vibrator to provide mechanical stimulus, or by transmitting stimulus to the device via a wired or wireless connection, such as a Bluetooth connection or a RF signal. In embodiments, where the device being tested is a hearing prosthesis, testing stimuli such as, but not limited to, a sweeped sine stimulus, noise (e.g., white, pink, a maximum length sequence ("MLS"), etc.), single tone, impulse, music, and/or speech may be provided using a speaker, head set, inbuilt generator, audio cable, or wireless streaming component of a portable device. While specific examples of testing stimulus are provided it will appreciated that the specific examples are provided for the purpose of illustration. As noted, other types of devices may be tested using the method 500 that can require different types of testing stimulus. Any type of test or testing stimulus may be provided at operation 510 so long as the portable device has a component capable of providing the testing stimulus to a medical device that can utilize the stimulus.

In embodiments, while the testing is being performed at operation 510, flow can continue to optional operation 512 where the method 512 confirms placement of the device for testing. For example, a gyroscope or magnetometer can be used to determine whether the device has moved during testing. If the device has moved, the method 500 can adjust the testing stimulus to reduce the displacement of the device, stop testing and instruct the user to reset the device in the testing location, and/or adjust the testing stimulus to compensate for the movement of the device.

Flow continues to operation 514 where the method 500 records testing results from the device. In embodiments, the testing results can consist of output generated by the device in response to the testing stimulus. The testing results can be recorded using one or more components of a portable device. For example, testing results can be recorded using a gyroscope, microphone, accelerometer, magnetometer, touch-sensitive display, and/or camera that are part of the portable device. In another embodiment, the testing results can be recorded by receiving input from a user or another application or hardware device that reports the output from the medical device.

Upon recording the testing results, flow continues to operation 516 where the testing results are analyzed. In embodiments, the testing results can be analyzed by comparing the testing results to the provided stimulus to determine whether the medical device correctly received and/or responded appropriately to the testing stimulus. For example, the analysis at operation 516 can include identifying similarities and differences between the testing stimulus, the received testing results, and known references (for example, previous test results, known device conditions, specifications, and/or settings). The known references can be stored in a database that is resident on the portable device or stored in a remote device that communicates with the portable device. In embodiments, the analysis of operation 516 produces test results. The test results, in further embodiments, can be further analyzed to determine a suggested remedy to optimize or otherwise correct medical device behavior. In further embodiments, the analysis includes comparing testing results to previous test results of the particular medical device, to test results from similar medical device, or to test results generated by similar portable devices. Comparison to other results can be made to normalize and/or otherwise adjust the testing results recorded at operation 514.

In embodiments, the type of testing performed varies depending on the type of device being tested. For example, when testing a bone conduction device, diagnosis of an on-board signal generator (i.e., the vibrator) can be performed by muting the medical device and ordering it to emit sinus waveforms through a predetermined frequency sequence. The sound received by the portable device will then be scanned for the frequency with the highest energy, which will correspond to the resonance frequency. Note that due to the placement of the medical device on the portable device (e.g., the point of contact with the portable device) the resonance frequency may not be the same as measured with more sophisticated equipment, but it should be consistent between measurements. If this resonance frequency should differ during later measurements, the vibrator's characteristics have changed. This change indicates that the vibrator is faulty or may fail. A magnetometer can be used to eliminate faulty placement as the source of error, since it will react to the local changes in the magnetic field introduced by magnetic materials in the device's vibrator. While a specific example of analysis for a particular type of hearing prosthesis is provided, it will be appreciated that different types of analysis may be performed, depending on the characteristics of the medical device, without departing from the scope of the embodiments disclosed herein.

Flow continues to decision operation 518 where a determination is made as to whether the test should to be repeated and/or whether additional tests should be performed. For example, if the analysis of the testing results produced an incomplete diagnosis, the test can be repeated or different tests can be performed. If additional tests should be performed, flow branches YES to return to operation 510. However, if the analysis resulted in a complete diagnostic test, then flow branches NO to operation 520. While decision operation 518 is described as being performed after analysis operation 516, in other embodiments the decision to perform additional tests can be made before the analysis step. For example, the testing results recorded at operation 514 are incomplete, the decision to perform additional tests can be made at that time rather than after operation 516.

In embodiments, the decision made at operation 518 is based upon the type of testing being performed. For example, different tests can be performed based upon a recipient or user need. In one embodiment, a full test is performed that includes a full frequency sweep to identify the resonance peak of a hearing prosthesis. In other embodiments, a quick test is performed where a sweep around a previously measured resonance frequency is made to verify that it is still the peak. The quick test reduces measurement time and can be employed when the user does not have time to perform a full test. In embodiments, the type of test being performed (e.g., full or quick) is used in the decision operation 518.

At operation 520, results and suggested remedies from the analysis are presented to a device recipient or user. In one embodiment, the results are presented via the display of the portable device. In another embodiment, the results can be audibly provided using a speaker on the portable device. Alternatively or additionally, the results and suggestions can be transmitted to another device for storage and/or presentation. In other embodiments, the results include the determinations made by analyzing the testing results at operation 516. The testing results provided at operation 520 will vary depending on the type of medical device being tested and the type of testing being performed.

The suggested remedy to correct any problems identified by analysis of the testing results can be displayed using the portable device. For example, the suggested remedy can include instructions to the user on how to adjust the medical device settings to correct problems or provide optimal performance. In another embodiment, the method 500 can automatically perform the suggested remedy by transmitting instructions and/or settings to the medical device via a wired or wireless connection with the medical device.

Flow continues to operation 522 where the results of the analysis are stored. In one embodiment, the results can be stored locally on the device or transmitted to a remote device for storage thereon. The stored results can be compared to results from later tests of the medical device. The stored results can also be analyzed to adjust testing stimulus based upon medical device performance, the performance of the portable device, or can be analyzed to otherwise identify deficiencies in the testing procedure and/or optimize the testing procedure.

While embodiments of the method 500 are described as consisting of a discrete number of operations in a particular order, more or fewer operations may be performed without departing from the scope of the embodiments disclosed herein. Furthermore, the order of the operations can be adjusted without departing from the concepts described herein. Additionally, while operations of the method 500 have been described as being performed by particular components of a portable device, such components have been identified for illustrative purposes only. The operations described with respect to the method 500 may performed using components other than the exemplary components described herein.

Figure 6:
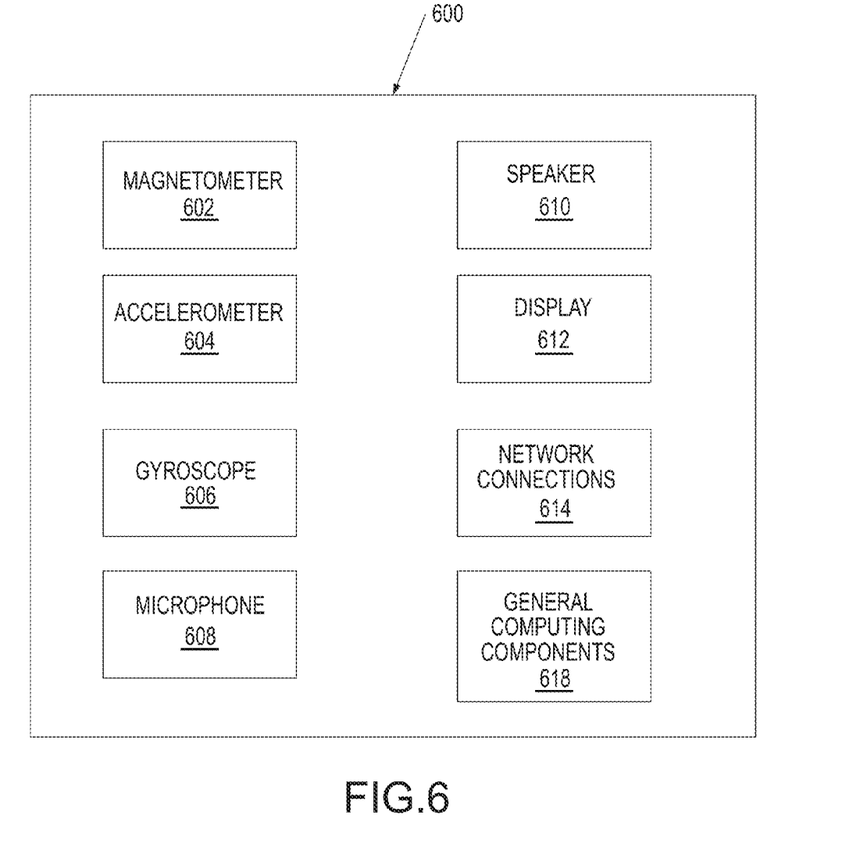
FIG. 6 illustrates components of an exemplary portable device 600.

FIG. 6 illustrates components of an exemplary portable device 600 that may be employed as a part of a system and/or to perform the methods disclosed herein. While the portable device 600 is described as having specific components, other portable devices having greater or fewer components that those described with respect to the portable device 600 can be used. The various components of the portable device 600 may be hardware components, software components, or a combination of hardware and software. The components described with respect to FIG. 6 may be utilized by the portable device 600 either individually or in combination to perform the operations described with respect to the method 500.

The portable device 600 includes at least one magnetometer 602, which can be used to confirm correct placement of a medical device for testing by identifying its location based upon a generated magnetic field. The magnetometer 602 can also be used to confirm that the device does not move during testing. In other embodiments, the magnetometer 602 is also used to detect device type by identifying different magnetic components of the device. The portable device 600 also includes at least one accelerometer 604 that can be used to measure vibrator-induced sound with less risk of interference than the microphone, but its relatively modest sample rate (about 100 Hz) makes it potentially less reliable for use other than as a signal strength indicator when the other properties of the received signal are already known. As such, the accelerometer 604 is particularly useful when used in combination with the microphone 608 to complement the recording of test results the medical device generates in response to the testing stimulus.

The portable device 600 can include at least one gyroscope 606 that can be used to ensure that the portable device 600 is placed on a flat surface for testing by measuring gravitational force (i.e., "G force"). The gyroscope 606 can also be used to measure accelerometer data. A microphone 608 can be used for high-accuracy measurement (e.g., for Fast Fourier transform ("FFT") analysis) but it is somewhat sensitive to external noise. In that case, measurement in quiet surroundings may result in more accurate results. Alternatively, the external microphone vent can be shielded, for example, by one of the fixtures described with respect to FIGS. 4A-4C, or even by a finger of the user. Covering the microphone vent has negligible impact on the sound received through casing vibrations but almost completely removes airborne sound. The portable device 600 may include at least one speaker 610 that can be used to provide audio testing stimulus or to provide audio instructions to the user. A device display 612 is used to display a user interface that provides information to the user regarding placement of the device for testing, information about testing results, displaying suggested remedies, and/or otherwise displaying a user interface that the user can interact with while performing the methods disclosed herein. While specific operations and/or tasks are identified as being performed by the various components described above, additional or different tasks can be performed by each component depending on the type of testing and/or type of medical device being tested. In embodiments, portable device 600 also includes network connections 614 and general computing components 618. For the sake of clarity, these components are described in more detail with respect to FIGS. 7 and 8.

Figure 7:
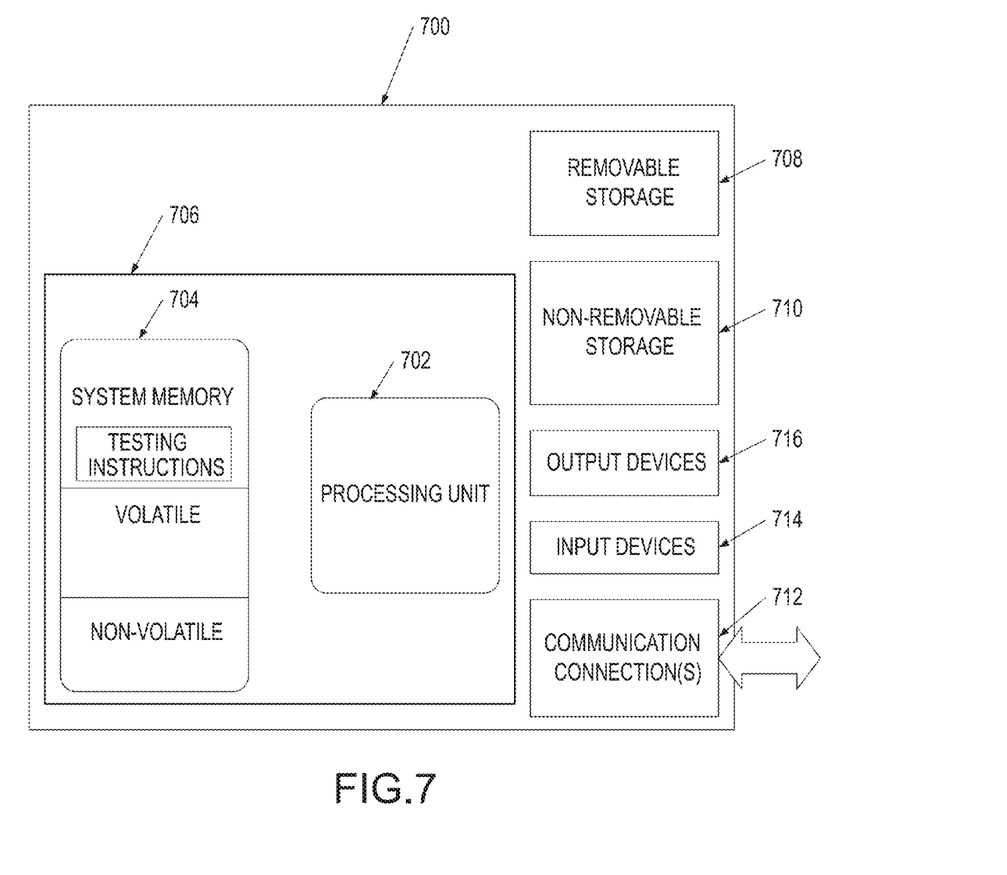
FIG. 7 illustrates one example of a suitable operating environment 700 in which one or more of the present examples may be implemented.

FIG. 7 illustrates one example of a suitable operating environment 700 in which one or more of the present embodiments may be implemented. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 700 typically includes at least one processing unit 702 and memory 704. Depending on the exact configuration and type of computing device, memory 704 (storing, among other things, instructions to perform the device testing methods described herein) may be volatile (such as RAM), non-volatile (such as ROM, flash memory, etc.), or some combination of the two. This most basic configuration is illustrated in FIG. 7 by dashed line 706. Further, environment 700 may also include storage devices (removable, 708, and/or non-removable, 710) including, but not limited to, magnetic or optical disks or tape. Similarly, environment 700 may also have input device(s) 714 such as touch screens, keyboard, mouse, pen, voice input, etc. and/or output device(s) 716 such as a display, speakers, printer, etc. Also included in the environment may be one or more communication connections, 712, such as LAN, WAN, point to point, Bluetooth, RF, etc.

Operating environment 700 typically includes at least some form of computer readable media. Computer readable media can be any available media that can be accessed by processing unit 702 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 700 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

In some embodiments, the components described herein comprise such modules or instructions executable by computer system 700 that may be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 700 is part of a network that stores data in remote storage media for use by the computer system 700.

Figure 8:
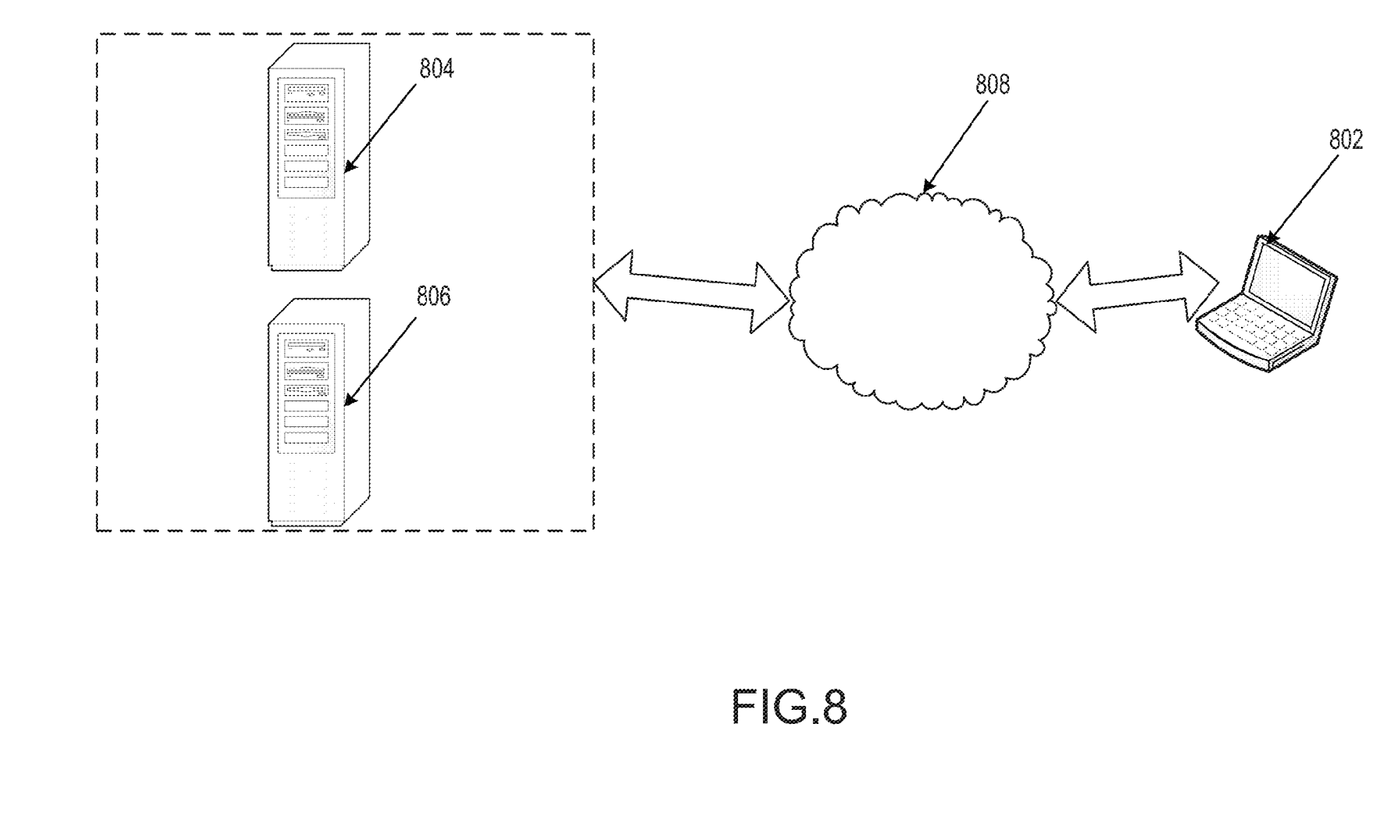
FIG. 8 is an embodiment of a network 800 in which the various systems and methods disclosed herein may operate.

FIG. 8 is an embodiment of a network 800 in which the various systems and methods disclosed herein may operate. In embodiments, portable device, such as client device 802, may communicate with one or more servers, such as servers 804 and 806, via a network 808. In embodiments, a client device may be a laptop, a tablet, a personal computer, a smart phone, a PDA, a netbook, or any other type of computing device, such as the portable device in FIG. 6 and the computing device in FIG. 7. In embodiments, servers 804 and 806 may be any type of computing device, such as the computing device illustrated in FIG. 7. Network 808 may be any type of network capable of facilitating communications between the client device and one or more servers 804 and 806. Examples of such networks include, but are not limited to, LANs, WANs, cellular networks, and/or the Internet.

In embodiments, the various systems and methods disclosed herein may be performed by one or more server devices. For example, in one embodiment, a single server, such as server 804 may be employed to perform the systems and methods disclosed herein. Portable device 802 may interact with server 804 via network 808 in send testing results from the device being tested for analysis or storage. In further embodiments, the portable device 802 may also perform functionality disclosed herein, such as by collecting and analyzing testing data.

In alternate embodiments, the methods and systems disclosed herein may be performed using a distributed computing network, or a cloud network. In such embodiments, the methods and systems disclosed herein may be performed by two or more servers, such as servers 804 and 806. Although a particular network embodiment is disclosed herein, one of skill in the art will appreciate that the systems and methods disclosed herein may be performed using other types of networks and/or network configurations.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure described some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method comprising:
   confirming placement of a medical device on a test location of a portable device, wherein the medical device comprises a bone conductor connected to a fixture;
   recording, with one or more sensors associated with the portable device, a response data generated by the medical device in response to a testing stimulus;
   analyzing the response data to produce a diagnostic result; and
   providing the diagnostic result to a user.

2. The method of claim 1, further comprising sending at least one of the diagnostic result, the response data, and the testing stimulus to a remote database.

3. The method of claim 1, wherein analyzing the response data comprises comparing the response data to the testing stimulus.

4. The method of claim 1, wherein the one or more sensors comprise at least one of a microphone and an accelerometer, wherein the microphone and the accelerometer are components of the portable device.

5. The method of claim 1, wherein providing the diagnostic result further comprises:
   displaying the diagnostic result; and
   displaying a suggested remedy.

6. The method of claim 1, wherein the portable device comprises one of:
   a smartphone; and
   a tablet.

7. The method of claim 1, further comprising providing the testing stimulus to the medical device via an output from the portable device.

8. The method of claim 7, wherein providing the testing stimulus comprises playing an audible testing stimulus using a speaker that is part of the portable device.

9. The method of claim 1, wherein the testing stimulus is generated by an on board signal generator of the medical device.

10. An apparatus comprising:
    a body comprising a vibration-conductive material, wherein the body comprises a contacting surface for contacting a surface of a portable device, and wherein the body comprises an interface for contacting at least a portion of a hearing prosthesis, and wherein the body comprises a substantially U-shaped channel adapted to receive therein at least a portion of an edge of the portable device.

11. The apparatus of claim 10, wherein the contacting surface comprises at least one of an adhesive, a friction interface, and a suction element.

12. The apparatus of claim 10, further comprising a clamp adapted to secure the fixture to the portable device.

13. The apparatus of claim 10, further comprising a cover adapted to cover a microphone of the portable device.

14. The apparatus of claim 13, wherein the cover comprises a projection extending from the body.

15. The apparatus of claim 10, wherein the interface defines a receiver for receiving at least a portion of a hearing prosthesis.

16. The apparatus of claim 15, wherein the receiver comprises a bone conduction element.

17. A system comprising:
    a portable device comprising:
       at least one processor; and
       computer storage media encoding computer executable instructions that, when executed by the at least one processor, perform a method comprising:

initiating a diagnostic test of a medical device;

recording, with one or more sensors associated with the portable device, a response data generated by the medical device in response to a testing stimulus;

analyzing the response data to produce a diagnostic result; and providing the diagnostic result to a user; and a fixture for interfacing the medical device with the portable device, the fixture comprising:

a body comprising a vibration-conductive material, wherein the body comprises a contacting surface for contacting a surface of the portable device, and wherein the body comprises an interface for contacting at least a portion of the medical device.

18. The system of claim 17, wherein the fixture comprises at least one of an adhesive, a friction interface, and a clamp.

19. The system of claim 17, wherein the medical device comprises a bone conduction device.

20. The system of claim 17, wherein the fixture includes a cover adapted to cover a microphone of the portable device.

21. The system of claim 20, wherein the cover is removable from the fixture.

22. A method comprising:

confirming placement of a medical device on a test location of a portable device;

recording, with one or more sensors associated with the portable device, a response data generated by the medical device in response to a testing stimulus, wherein the testing stimulus is generated by an on board signal generator of the medical device analyzing the response data to produce a diagnostic result; and providing the diagnostic result to a user.

23. The method of claim 22, further comprising sending at least one of the diagnostic result, the response data, and the testing stimulus to a remote database.

24. The method of claim 22, wherein analyzing the response data comprises comparing the response data to the testing stimulus.

25. The method of claim 22, wherein the one or more sensors comprise at least one of a microphone and an accelerometer, wherein the microphone and the accelerometer are components of the portable device.

26. The method of claim 22, wherein providing the diagnostic result further comprises:

displaying the diagnostic result; and displaying a suggested remedy.

27. The method of claim 22, wherein the portable device comprises one of:

a smartphone; and a tablet.

28. The method of claim 22, further comprising providing the testing stimulus to the medical device via an output from the portable device.

29. The method of claim 28, wherein providing the testing stimulus comprises playing an audible testing stimulus using a speaker that is part of the portable device.

30. The method of claim 22, wherein the medical device comprises a bone conductor connected to a fixture.

* * * * *